(12) United States Patent
Smith et al.

(10) Patent No.: US 6,821,479 B1
(45) Date of Patent: Nov. 23, 2004

(54) PRESERVATION OF BIOLOGICAL MATERIALS USING FIBER-FORMING TECHNIQUES

(75) Inventors: Daniel J. Smith, Stow, OH (US); Woraphon Kataphinan, Akron, OH (US); Darrell H. Reneker, Akron, OH (US); Sally Dabney, Akron, OH (US)

(73) Assignee: The University of Akron, Akron, OH (US)

( * ) Notice: Subject to any disclaimer, the term of this patent is extended or adjusted under 35 U.S.C. 154(b) by 426 days.

(21) Appl. No.: 09/879,386

(22) Filed: Jun. 12, 2001

(51) Int. Cl.⁷ .............................................. B01D 17/00

(52) U.S. Cl. ................................. 422/1; 422/40; 623/1

(58) Field of Search ........................... 422/1, 40; 623/1

(56) References Cited

U.S. PATENT DOCUMENTS

| | | | |
|---|---|---|---|
| 4,044,404 A | 8/1977 | Martin et al. | ..................... 3/19 |
| 4,054,625 A | 10/1977 | Kozlowski et al. | ........... 264/13 |
| 4,323,525 A | 4/1982 | Bornat | ........................ 264/24 |
| 5,522,879 A | 6/1996 | Scopelianos | ................... 623/1 |

FOREIGN PATENT DOCUMENTS

| | | |
|---|---|---|
| WO | WO 98/03267 | 1/1998 |

*Primary Examiner*—Krisanne Jastrzab
(74) *Attorney, Agent, or Firm*—Roetzel & Andress

(57) ABSTRACT

A method of preserving a biological material includes the steps of providing at least one fiber-forming material, mixing at least one biological material, and optionally, one or more additives, to the at least one fiber-forming material to form a mixture, and forming at least one fiber from the mixture, wherein the resulting fiber has a diameter between 0.3 nanometers and about 25 microns. A biological material preserved by this method is also disclosed.

22 Claims, 10 Drawing Sheets

PRESERVATION OF BIOLOGICAL MATERIALS USING FIBER-FORMING TECHNIQUES

BACKGROUND OF THE INVENTION

Biological materials may be preserved for long term storage by a number of techniques including storage at low temperatures and freeze-drying. Storage at low temperature, while effective, is limited to applications where constant refrigeration is available. The need for constant refrigeration limits the usefulness of this technique. Preservation of biological samples by freeze-drying, however, is not so limited.

The technique of freeze-drying, also known as lyophilization, involves the freezing of a sample, forming water crystals, followed by the direct sublimation of the water crystals, usually under vacuum. That is, the water is directly converted from a solid state to a gaseous state without passing through a liquid state. Freeze-drying, therefore, typically dehydrates a sample without denaturing or otherwise altering its three-dimensional structure by heating. Once freeze-dried, samples are often stable at room temperature for an extended period of time provided that the samples are stored in a water-vapor impermeable container, such as, for example, a glass ampule. Therefore, freeze-drying provides a method of long term storage of biological materials at room temperature.

Freeze-drying, however, has disadvantages associated with it. Freeze-drying requires both time and expensive equipment. Freeze-drying can also cause irreversible changes to occur in some proteins or other samples by mechanisms other than those associated with heating. Among these changes are denaturation caused by a change in pH or by the concentration of other substances near the molecules of the biological material. Therefore, there is a need for a method of preservation of biological materials that provides an alternative to freeze-drying. Such a need is acutely felt with regard to the delivery of biological materials to remote areas requiring long transport times with little or no refrigeration available. The delivery of vaccines or other medical products to remote areas is one specific example of such a need. Ideally, such a method would provide an economical method for long term preservation of such samples at room temperature.

The technique of electrostatic spinning, also known within the fiber forming industry as electrospinning, of liquids and/or solutions capable of forming fibers, is well known and has been described in a number of patents, such as, for example, U.S. Pat. Nos. 4,043,331 and 5,522,879. The process of electrostatic spinning generally involves the introduction of a liquid into an electric field, so that the liquid is caused to produce fibers. These fibers are generally drawn to a conductor at an attractive electrical potential for collection. During the conversion of the liquid into fibers, the fibers harden and/or dry. This hardening and/or drying may be caused by cooling of the liquid, i.e., where the liquid is normally a solid at room temperature; by evaporation of a solvent, e.g., by dehydration (physically induced hardening); or by a curing mechanism (chemically induced hardening). The process of electrostatic spinning has typically been directed toward the use of the fibers to create a mat or other non-woven material, as disclosed, for example, in U.S. Pat. No. 4,043,331. In other cases, electrospinning is used to form medical devices such as wound dressings, vascular prostheses, or neural prostheses as disclosed, for example, in U.S. Pat. No 5,522,879.

In still other cases, electrospinning is used to create fibers which act as a carrier for the delivery of therapeutic compounds, as disclosed, for example, in co-pending U.S. patent application Ser. No. 09/571444, filed on May 16, 2000. Such examples of electrospinning with therapeutic compounds involve immediate delivery of the electrospun material. Other uses of electrospinning to deliver therapeutic compounds have suggested the formation of a fiber which contains a core component and a coating component. In one example, provided in PCT/GB97/01968, a biologically active ingredient may be contained within a core of a fiber, fibril, or microcapsule. The active ingredient is released from the ends of the fiber or fibril, through the coating material if the coating material is permeable to the active component, or by enzymatic, physical, or chemical disruption of the coating, such as biodegradation or the application of pressure to the fiber. Such a fiber structure allows the biological material to remain in liquid form within the fiber. Such fibers may be used for a controlled release of the biologically active component. While electrospinning has been used to deliver therapeutic compounds, heretofore, electrospinning has not been used to preserve biological materials.

BRIEF SUMMARY OF THE INVENTION

It is, therefore, an aspect of the present invention to provide a method of preserving biological material.

It is another aspect of the present invention to provide a method of preserving biological materials, as above, that is an alternative to freeze-drying.

At least one or more of the forgoing aspects, together with the advantages thereof over the prior art relating to the preservation of biological material, which shall become apparent from the specification which follows, are accomplished by the invention as hereinafter described and claimed.

In general, the present invention provides a method of preserving biological material which includes the steps of providing at least one fiber-forming material, mixing at least one biological material, and optionally, one or more additives, to the at least one fiber-forming material to form a mixture, and forming a fiber from the mixture wherein the fiber has a diameter between about 0.3 nanometers and 25 microns.

DETAILED DESCRIPTION OF THE INVENTION

Figure 1:
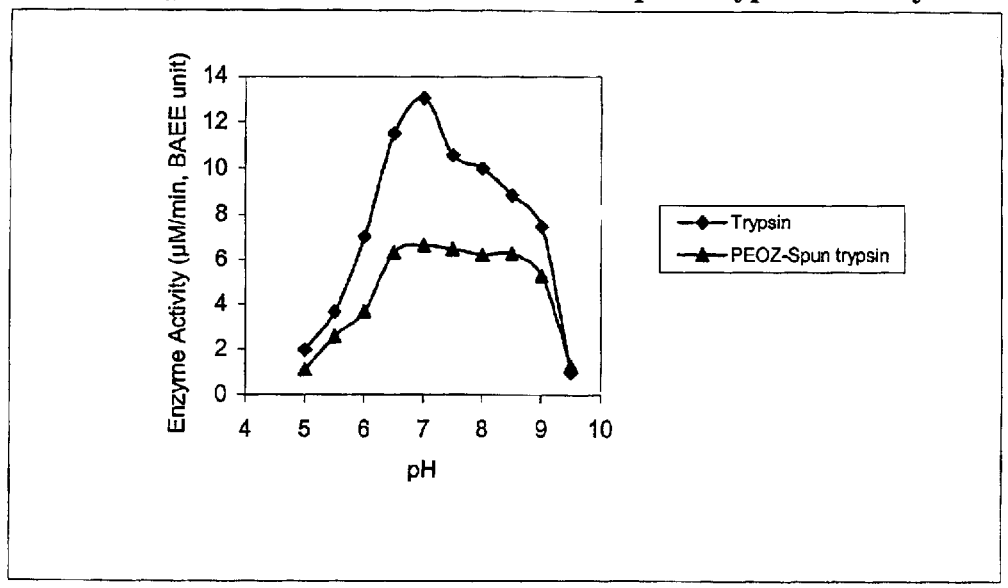
FIG. 1 is a graph showing the pH dependence of native and PEOZ-spun trypsin activity.

As mentioned above, the present invention is directed toward a method of preserving biological material by forming a fiber from a mixture comprising a biological material and a fiber forming material to produce fibers containing the at least one biological material in a preserved state. In those instances where the biological material is capable of forming fibers itself, the biological material may function as both the fiber forming material and the preserved biological sample.

The mixture of biological material and fiber-forming material may be formed into fibers by any method which does not negatively affect the activity of the biological material such as by heating, for example. Such methods include electrospinning and the "Nanofibers by Gas Jet" or NGJ technique disclosed in co-pending application Ser. No. 09/410,808, filed on Oct. 1, 1999.

Electrospinning generally involves the introduction of a polymer or other fiber-forming liquid into an electric field, so that the liquid is caused to produce fibers. These fibers are drawn to an electrode at a lower electrical potential for collection. During the drawing of the liquid, the fibers rapidly harden and/or dry. The hardening/drying of the fibers may be caused by cooling of the liquid, i.e., where the liquid is normally a solid at room temperature; by evaporation of a solvent, e.g., by dehydration (physically induced hardening); by a curing mechanism (chemically induced hardening); or by a combination of these methods. Electrostatically spun fibers can be produced having very thin diameters.

It will be appreciated that, because of the very small diameter of the fibers, the fibers have a high surface area per unit of mass. This high surface area to mass ratio permits fiber-forming material solutions to be transformed from solvated fiber-forming materials to solid nanofibers in fractions of a second. When biological materials are dissolved or suspended in a fiber-forming material solution which is then formed into fibers, the samples experience a rapid loss of excess solvent. This invention thereby also provides a fiber containing a substantially homogeneous mixture of at least one fiber-forming material and at least one preserved biological material. While not wishing to condition patentability on any particular theory of operation, it is believed that in the same time interval in which destabilizing changes such as changes in pH or concentration occur, these samples become embedded in a fiberous polymer matrix which immobilizes and protects the sample. Alternatively or in addition, at least a portion of the biological sample embedded in the matrix may reversibly denature to some degree and renature in an active conformation upon rehydration. It is believed, therefore, that the fiber of the present invention contains biological material embedded in a dry protective matrix. It should be understood however, that while the fiber is described herein as being "dry", the biological material may retain a certain amount of water provided that the water present does not interfere with the solidification of the fiber. That is, formation of a dry fiber should be understood as not precluding the association of water of hydration with the biological sample to form a hydrate solid.

The at least one fiber-forming material used in this invention may be selected from any fiber-forming material which can be dissolved and is otherwise compatible with the biological material to be preserved. Fiber-forming materials which may be used in the practice of the method of the present invention include water soluble polymers, for example. In particular, acceptable fiber-forming materials, by way of example and not of limitation, include poly(vinyl pyrrolidone) (PVP), polyethyl oxazoline (PEOZ), polyethylenimine (PEI), polyethylene oxide (PEO) and mixtures thereof.

It is envisioned that the present invention will typically be used to preserve a biological material for later use. Upon completion of the preservation period, the biological material is recovered from the fiber for example, by mixing the fiber in a solvent for the fiber-forming material. Any solvent may be used, provided that the solvent is compatible with the preserved biological material. Other methods for recovering the biological material from the fiber are also envisioned. These include biodegradation, hydrolysis, thermal melting or other depolymerization of the fiber forming material. Upon recovery, the biological material must possess at least a portion of its original biological activity. Preferably, the biological material preserved in the fiber of the present invention should retain at least 25, 30, 40, 50, 60, 70, 80 or even 90 percent of its activity when stored at room temperature (approximately 20–25° C.) for at least 12 hours, 24 hours, 48 hours, 1 week, 15 days, 1 month, or even 6 months.

Biological materials which may be a component of the fiber of the present invention generally include, by way of example and not of limitation, proteinaceous compounds, carbohydrates, nucleic acids and mixtures thereof.

Non-limiting examples of proteinaceous compounds which may be utilized in the fiber of the present invention include peptides, polypeptides, proteins, enzymes, coenzymes, holoenzymes, enzyme subunits, and prions. Enzymes which may be used include peroxidase, trypsin, and thrombin, although other enzymes may also be used. The fiber of the present invention maybe spun to form mats of fiber containing at least one fiber-forming material and at least one biological material. When thrombin or any other medically useful protein is utilized, it is envisioned that the fiber of the present invention may be a component of a medical dressing or other medical device. It is also envisioned that other therapeutic compounds, including therapeutic peptides or polypeptides, may be present in the fiber. Examples include viral fusion inhibitors, hormone antagonists, and other compounds which exert a therapeutic effect by binding with a receptor molecule in vivo.

A non-limiting example of a carbohydrate that may be utilized in the present invention includes dextran. One or more carbohydrates such as glucose, fructose, or lactose, for example, may also be present to act as a stabilizer of another biological material such as an enzyme or other protein. Other additives, such as, for example, polyethylene glycol, may also be present.

Non-limiting examples of nucleic acids include ribonucleic acids and deoxyribonucleic acids. This includes ribonucleic acids such as anti-sense ribonucleic acid sequences and ribozymes, and deoxyribonucleic acids such as oligonucleotides, gene fragments, natural and artificial chromosomes, plasmids, cosmids, and other vectors.

It is also envisioned that the at least one biological material may be a mixed sample containing more than one type of biological material. Additionally, the at least one biological material may be labeled with a marker such as, for example, a radioactive marker, a fluorescent marker, or a gold or other high atomic number particle which is visible by electronmicroscopy.

It is also envisioned that the at least one biological material may be a material that is capable of acting as an antigen by eliciting an immune response by an individual when exposed to the biological material. When this is the case, the biological material preserved by the present invention may also be a component of a vaccine. It is envisioned that in such an embodiment, a medically acceptable fiber-forming material may be used to preserve the antigen for later rehydration and use as a vaccine. In general, rehydration of the fiber of the present invention may be accomplished by mixing the fiber with a solvent for the fiber-forming material. When the fiber is used to preserve an antigen for use in a vaccine, the solvent will optimally be a medically acceptable compound. Depending on the antigen and rehydration solution used, the resulting vaccine may be an injectible or an ingestible vaccine. Other medically acceptable administration techniques may also be used with the resulting vaccine.

The present invention may also be used to produce a component of a test kit in which the preserved biological material may be subsequently used in performing a function of the kit. Non-limiting examples of such a kit include test kits which may be used to determine the presence of a specific chemical or biological compound in a test material. Such a kit may be used, for example, to test for the presence of a specific metabolite or other compound in a blood, serum, urine or other fluid sample from an individual for clinical or forensic purposes. Other sources of test material might also be used with such a kit. Such a kit may also be used to determine the presence of chemical compounds in environmental samples, for example. It is envisioned that more than one biological material may be preserved together in such a kit. For example, an enzyme and coenzyme or cofactor for a particular reaction may be preserved either in separate fibers or in the same fiber.

The relative amounts of fiber-forming material and biological material that may be present in the fiber of the present invention may vary. In one embodiment, the biological material comprises between about 1 and about 12 percent by weight to volume (w/v) of the mixture from which the fiber is electrospun. In another example, the biological material comprises 1 percent of the mixture or less. In still another example, the biological material may be 0.25 percent, 0.5 percent, 0.75 percent, or 1.0 percent of the mixture by weight to volume. It is envisioned that larger or smaller concentrations of biological material may also be utilized.

As mentioned above, fibers spun electrostatically can have a very small diameter. These diameters may be as small as 0.3 nanometers and are more typically between 3 nanometers and about 25 microns. Preferably, the fiber diameters are on the order of about 100 nanometers to about 25 microns, and more preferably, on the order of about 100 nanometers to about 1 micron. Such small diameters provide a high surface area to mass ratio, preferably on the order of about 300 $m^2/g$. Within the present invention, a fiber may be of any length. The term fiber should also be understood to include particles that are drop-shaped, flat, or that otherwise vary from a cylindrical shape.

As mentioned above, the process of electrostatic spinning generally involves the introduction of a liquid into an electric field, so that the liquid is caused to produce fibers. These fibers are generally drawn to an electrode for collection. During the drawing of the liquid, the fibers harden and/or dry. This hardening and/or drying may be caused by cooling of the liquid, i.e., where the liquid is normally a solid at room temperature; by evaporation of a solvent, e.g., by dehydration (physically induced hardening); or by a curing mechanism (chemically induced hardening). The hardened fibers are collected on a receiver such as, for example, a polystyrene or polyester net or a foil slide. As one skilled in the art will recognize, the fibers may be spun using a wide variety of conditions such as potential difference, flow rate, and gap distance. These parameters will vary with conditions such as humidity or other environmental conditions, the size of the biological material or other additive, the solution viscosity, the collection surface, and the polymer conductivity, among others.

The at least one fiber-forming material is in a liquid state when it is electrospun with the biological material to form a fiber containing a mixture of the at least one fiber-forming material and the at least one biological material. Mixtures of the at least one fiber-forming material and at least one biological material include mixtures where the biological material is soluble in the at least one fiber-forming material in its liquid state and those mixtures in which the at least one biological material is insoluble in the at least one fiber-forming material in its liquid state. When the biological material is insoluble in the at least one fiber-forming material in its liquid state, the biological material may take the form of a suspension in the fiber-forming material. Whether the biological material is soluble or insoluble in the fiber-forming material, the biological material and the fiber-forming material may be mixed by any method which forms a substantially homogeneous mixture, including, for example, mechanical shaking or stirring, although other methods may be used. As one skilled in the art will recognize, solubility of the biological material in the fiber-forming material solution will depend on the characteristics of the material itself, as well as factors such as, for example, the requirements of the material for a specific pH range, osmolarity, or the presence of co-factors for the material.

In order to demonstrate the practice of the present invention, various fibers containing at least one fiber-forming material and at least one biological material were made. Several of these fibers were tested for activity of the biological material after electrospinning of the fibers. The following examples should not be viewed as limiting the scope of the invention. The claims will serve to define the inventions.

Peroxidase activity was determined neat and after being electrospun with a polymer. Activity of peroxidase was determined by measuring an increase in the absorbance of a solution at 470 nm resulting from the decomposition of hydrogen peroxide in the presence of guaiacol as a hydrogen donor. The assay buffer contained 50 mM potassium phosphate buffer pH 6.5, 2 mM hydrogen peroxide, and 20 mM Guaiacol.

The total volume of the reaction was 2 ml; the absorbance was read at a wavelength of 470 nm at 25° C. The protein concentration of samples was determined by the Biuret method. Enzyme activity data is shown in Table 1.

TABLE 1

Peroxidase Activity Before Electrospinning

| Sample | Enzyme activity ($\Delta$A470/min/mg/ml) |
|---|---|
| 1 | 119 |
| 2 | 315 |
| 3 | 270 |
| Mean ± SD | 235 ± 84 (n = 3) |

Peroxidase was dehydrated by electrospinning in polyethyl oxazoline (PEOZ) in the following manner. 1 mg of peroxidase was dissolved in 3 ml of 28 percent (w/v) polymer solution. The sample was electrospun using a cone cap at room temperature, a voltage of 27 Kv, a current of 1.27 μA, and negative polarity. The gap distance was 6.5 inches (16.5 cm), and the sample was collected on a polyester net. A thin layer of fiber was collected. A thin layer of spun PEOZ containing peroxidase (about 10×10 cm) was dissolved in 2 ml of distilled water. This solution was assayed for peroxidase activity and protein concentration with appropriate dilutions as described above. Data for enzyme activity after electrospinning with PEOZ are shown in Table 2.

TABLE 2

Peroxidase Activity After Electrospinning with Polyethyl Oxazoline (PEOZ)

| Sample | Enzyme Activity ($\Delta$A470/min/mg/ml) |
|---|---|
| 1 | 60 |
| 2 | 67 |
| 3 | 103 |
| 4 | 128 |
| Mean ± SD | 90 ± 28(n = 4) |

The data demonstrate that peroxidase that was dehydrated by electrospinning exhibited approximately 38 percent of its original activity upon rehydradon in water (90/235×100=38 percent).

Trypsin was also used to test the method of preservation of the present invention. Except where noted otherwise, about 2.5 mg/ml (0.25% w/v) of trypsin in 2 ml of 26% w/v polymer solution was electrospun. When the samples were electrospun from PEOZ polymer solution, the electrospinning was performed using a cone cap at room temperature, a voltage of 22–25 KV, a current of 200–300 nA, and a positive polarity, except when noted otherwise. The gap distance was 23 cm, and the sample was collected on polyester net. When polymers others than PEOZ were used, the parameters of electrospinning process varied, as indicated below. Trypsin was typically reconstituted from the fiber by dissolving a piece of the formed trypsin-containing fiber in distilled water. The resulting solution was assayed for enzyme activity and protein concentration with appropriate dilutions. Except where noted otherwise, assays were performed at least in triplicate.

The enzymatic activity of trypsin was determined by measuring the increase in the absorbance of a solution at 253 nm resulting from the hydrolysis of benzoyl-L-arginine ethyl ester (BAEE). A 0.25 mM BAEE solution (3 ml) in 0.067 M phosphate buffer (pH 7.0) was used, and placed into a cell (10 mm path-length) of a UV spectrophotometer. When the temperature had equilibrated to 25° C., 200 μl (10 μg/ml) of native trypsin or enzyme solution rehydrated from enzyme-containing fibers was added, and the absorbance at 253 nm recorded versus time. One unit of the enzyme activity is defined as that amount of enzyme causing a change in absorbance of 0.001 per minute. The protein content was determined by measuring absorbance at 280 nm using a series of native trypsin samples as calibration standards.

Initial rates of hydrolysis of BAEE in 0.067 M phosphate buffer pH 7.0, at 25° C. were determined at eight substrate concentrations within the range 0.05–0.75 mM, with the enzyme concentration fixed at 0.625 μg/ml. The kinetic parameters $V_{max}$ and $K_m$ were determined, for both the native and PEOZ-spun trypsin, using a Line-Weaver-Burk plot. $K_{cat}$ was calculated using the equation $K_{cat}=V_{max}/E_o$, where $E_o$ is initial enzyme concentration. These values are shown in Table 3. As shown in Table 3, the catalytic efficiency of native and PEOZ-spun trypsin was approximately identical.

TABLE 3

Kinetic parameters for hydrolysis of BAEE for native and PEOZ-spun trypsin

| | $K_m$ (mM) | $V_{max}$ (mM/S) | $K_{cat}$ (S$^{-1}$) | $K_{cat}/K_m$ (S$^{-1}$mM$^{-1}$) (Efficiency) |
|---|---|---|---|---|
| Native trypsin | 0.117 ± 0.014 | 2.38 × 10$^{-4}$ ± 1.0 × 10$^{-5}$ | 9.078 | 77.64 |
| PEOZ-spun trypsin | 0.059 ± 0.012 | 1.30 × 10$^{-4}$ ± 6.7 × 10$^{-6}$ | 4.958 | 83.33 |

The influence of pH on native and PEOZ-spun trypsin activity was investigated at 25° C. with a fixed enzyme concentration (0.625 μg/ml) and 0.25 mM BAEE. Enzyme activity was determined as described above except two different buffer systems were used: 0.067 M Phosphate (pH 5.0–8.7), and 0.046 M Tris-HCl (pH 6.6–10). The activity of these samples at pH 5–10 was determined. The results are summarized in FIG. 1. As shown in FIG. 1, maximum reaction velocity occurred at a pH of about 7.0 with both native and PEOZ-spun trypsin.

Figure 2:
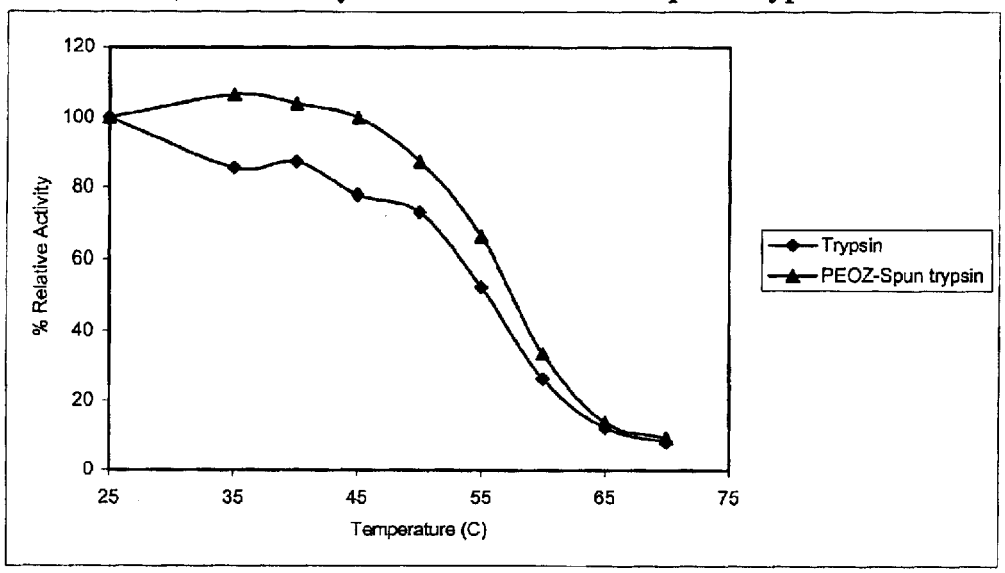
FIG. 2 is a graph showing the thermostability of native and PEOZ-spun trypsin.

Native and PEOZ-spun trypsin solutions of 0.3 ml at concentration of 0.05 mg/ml in phosphate buffer (0.067 M, pH 7.0) were incubated for 10 min at temperatures between 25 and 70° C. Samples were removed and cooled on ice for 1 min and residual activity assayed and compared with the activity of a sample incubated at 25° C. Assays were performed in triplicate in 0.067 M phosphate buffer, pH 7.0, containing 0.25 mM BAEE and 0.625 μg/ml trypsin in a final volume of 3.2 ml. The results are expressed in FIG. 2 as a percentage of residual activity as a function of the temperature, and show that electrospinning does not harm subsequent stability of PEOZ-spun trypsin.

A 4.2 percent w/w trypsin to polymer mixture was used as described above to determine the effect of polymer (PEOZ) on the trypsin activity assay and protein determination. This represents a 23.8 fold excess of polymer over enzyme (100/4.2=23.8). This factor was used in both the trypsin activity assay and protein determination.

Trypsin activity was determined by measuring the increase in absorbance of a solution at 253 nm resulting from the hydrolysis of BAEE. The activity of trypsin was measured in presence and absence of PEOZ without electrospinning. For samples tested in the presence of PEOZ, 0.0402 g of the polymer was added at the time of preparation to 100 ml of 0.046 M Tris-HCl buffer, pH 8.1 that contains 0.0115 M calcium chloride. The results obtained are summarized in Table 4.

TABLE 4

Trypsin Activity in the Presence and Absence of PEOZ

| Sample | Enzyme activity − PEOZ ($\Delta$A253/min/mg/ml) | Enzyme activity + PEOZ ($\Delta$A253/min/mg/ml) |
|---|---|---|
| 1 | 1.75 | 1.92 |
| 2 | 1.40 | 1.92 |
| 3 | 1.75 | 1.40 |
| 4 | 1.57 | 1.57 |
| 5 | — | 1.57 |
| Mean ± SD | 1.61 ± 0.15(n = 4) | 1.68 ± 0.21(n = 5) |

These results indicate that PEOZ does not significantly interfere with the trypsin activity assay.

the protein concentrations of standard samples were measured in the presence and absence of PEOZ by the Biuret method. For protein standards with PEOZ present, 0.201 g of polymer was added at the time of preparation to 50 ml of standard protein. Additionally, a 0.4 percent solution of PEOZ without protein was used to determine whether PEOZ interferes with the total protein determination assay. As shown in Table 5, PEOZ does not significantly affect protein concentration determination.

TABLE 5

Protein Concentration Determinations

| Sample | Protein Conc. (mg/ml) |
|---|---|
| PEOZ (polymer) | 10.2 ± 1.1 (n = 3) |
| Protein | 366.5 ± 14.6 (n = 6) |
| Protein + PEOZ | 371.3 ± 24.3 (n = 6) |

Figure 3:
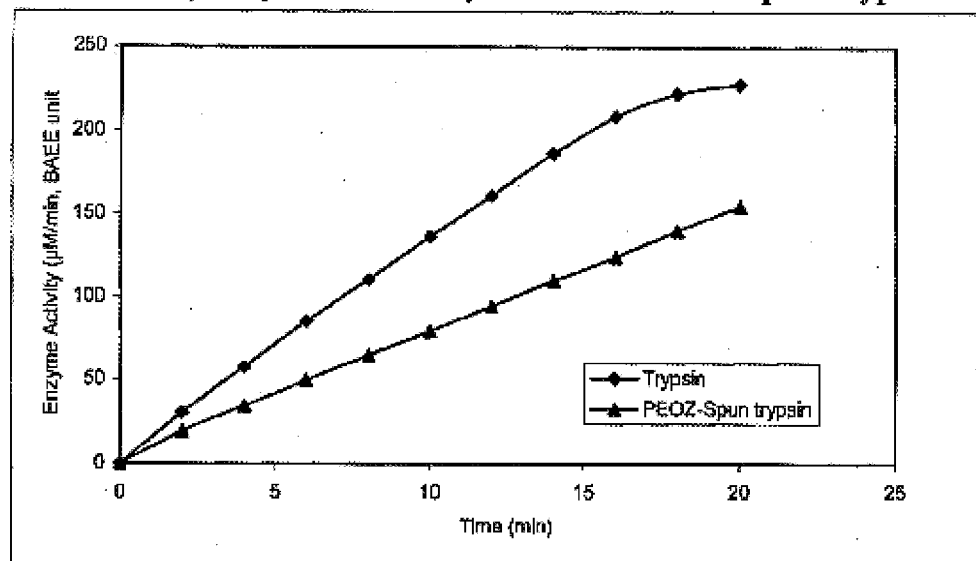
FIG. 3 is a graph showing the rate of hydrolysis of BAEE with time by native and PEOZ-spun trypsin.

The relationship between the enzyme activity and enzyme concentration of native and PEOZ-spun trypsin was determined. The experiment was performed with enzyme concentrations varying from 0.1 to 6.25 $\mu$g/ml; results indicated that enzyme activity was linear with enzyme concentration (not shown). The hydrolysis of BAEE by native and PEOZ-Spun trypsin was followed over time using 0.625 $\mu$g/ml trypsin under the assay conditions described above. The results are shown in FIG. 3. As shown in FIG. 3, the rate of hydrolysis of BAEE was linear with time for both samples.

Figure 4:
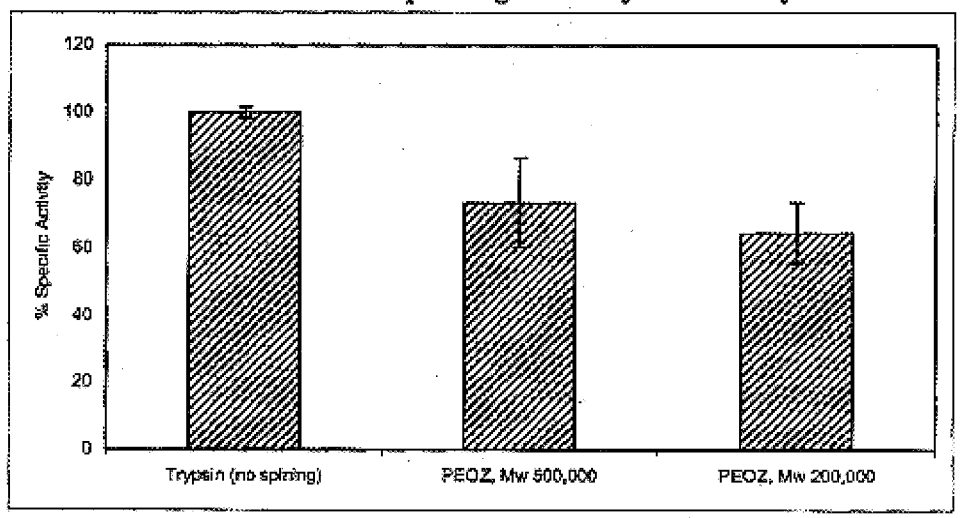
FIG. 4 is a graph showing the effect of electrospinning on the activity of trypsin.

The catalytic activity of native and PEOZ-spun trypsin was investigated under the same conditions. About 0.25% w/v trypsin (2.5 mg/ml) in 26% w/v polymer solution was electrospun using a cone cap at room temperature, a voltage of 22 KV, a current of 270 nA, and positive polarity. The gap distance was 23 cm, and the sample was collected on a polyester net. A small piece of trypsin-containing fiber was dissolved in distilled water, and then this solution was used in investigation of enzyme assay, and protein determination with appropriate dilutions. Studies were performed with PEOZ of two different molecular weight (Mw 500,000 and Mw 200,000), and the residual enzyme activity, expressed as a percent of the rate obtained for the native trypsin, is plotted in FIG. 4 as a function of the molecular weight (Mw) of PEOZ that was used in electrospinning. Assays were performed in 0.067 M phosphate buffer, pH 7.0, containing 0.25 mM BAEE and 0.625 $\mu$g/ml trypsin in a final volume of 3.2 ml, as described above. The values shown in FIG. 4 are means±SD. PEOZ (500,000)-spun trypsin gave slightly higher residual activity than PEOZ (200,000)-spun trypsin.

Figure 5:
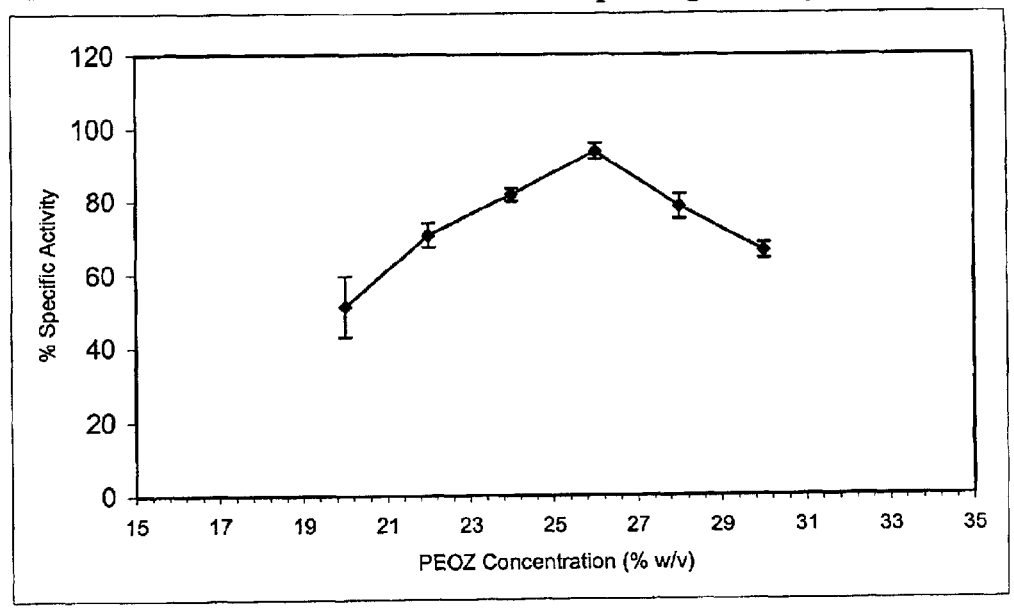
FIG. 5 is a graph showing the effect of PEOZ concentration on enzyme activity.

Six different concentrations of PEOZ (20%, 22%, 24%, 26%, 28%, and 30% w/v) were used in the preparation of enzyme-containing PEOZ solution, which were then used in the electrospinning. A fixed trypsin concentration of 0.25% w/v (2.5 mg/ml) was used in each preparation, and the electrospining was done under the conditions described above. A 26% of PEOZ gave the best retaining trypsin activity, as shown in FIG. 5. It was noticed that the electrospinning process was more difficult at the low PEOZ concentrations (20–24% w/v), as well as the high PEOZ concentrations (28–30% w/v). It is believed that these difficulties were due to the viscosities of these samples being either lower or higher than is optimal for electrospinning.

Figure 6:
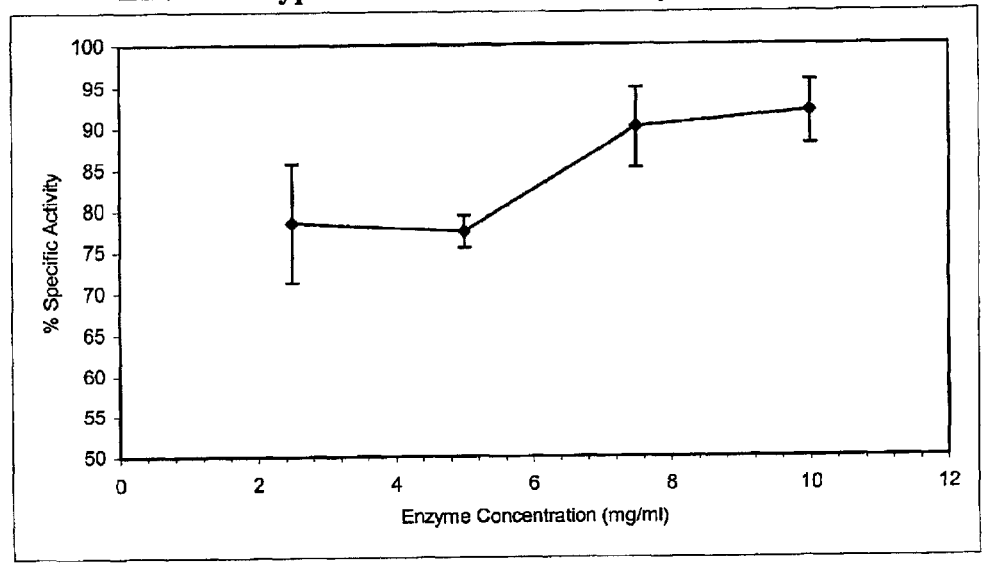
FIG. 6 is a graph showing the effect of trypsin concentration on enzyme activity.

Four different concentrations of trypsin (2.5, 5, 7.5, and 10 mg/ml) were used in the preparation of enzyme-containing PEOZ solutions, which were used in electrospinning. A fixed PEOZ concentration of 26% w/v was used in each preparation, and the electrospinning was performed as described above. In FIG. 6, the residual enzyme activity, expressed as a percent of the activity obtained for the native trypsin, is plotted as a function of concentration of trypsin that has been used in electrospinning. As trypsin concentration in the enzyme-containing PEOZ solution increased, the retained trypsin activity recovered from an electrospun fiber sample improved.

Figure 7:
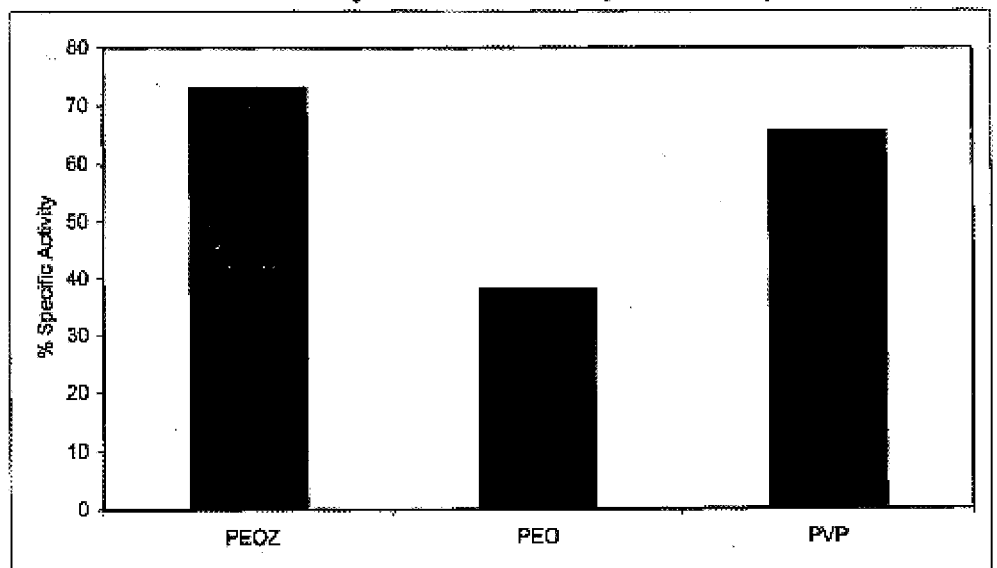
FIG. 7 is a graph showing the effect of the polymer used in electrospinning on enzyme activity.

Polyethylene oxide (PEO) (Mw 400,000), and polyvinylpyrrolidone (PVP) (Mw 360,000) were also used as polymer substrates for the electrospinning of fibers containing typsin. In case of PEO, about 0.25% w/v (2.5 mg/ml) trypsin in 6% w/v polymer solution was used in electrospinning the sample. A cone cap was used to do the spinning at room temperature, using a voltage of 14 KV, a current of 80 nA, and positive polarity. The gap distance was 28.5 cm, and the sample was collected on polyester net. PVP fibers were electrospun from a solution containing about 0.25% w/v (2.5 mg/ml) trypsin in 22% w/v polymer. A cone cap was used to do the spinning at room temperature, using a voltage of 22 KV, a current of 360 nA, and positive polarity. The gap distance was 23 cm, and the sample was collected on a polyester net. A piece of each trypsin-containing fiber was dissolved in distilled water, and the solutions were tested for enzyme activity and protein concentration with appropriate dilutions. In FIG. 7, the enzyme stability from solutions made from these polymer fibers is compared to the stability from solutions made from PEOZ fibers. The residual enzyme activity, expressed as a percentage of the activity obtained for native trypsin, is plotted as a function of polymer type that was used in electrospinning. As shown in FIG. 7, trypsin recovered from PEOZ fibers retained greater than 70 percent activity while trypsin recovered from PVP fibers retained approximately 65 percent activity and trypsin recovered from PEO fibers retained approximately 40 percent activity compared to native enzyme.

Figure 8:
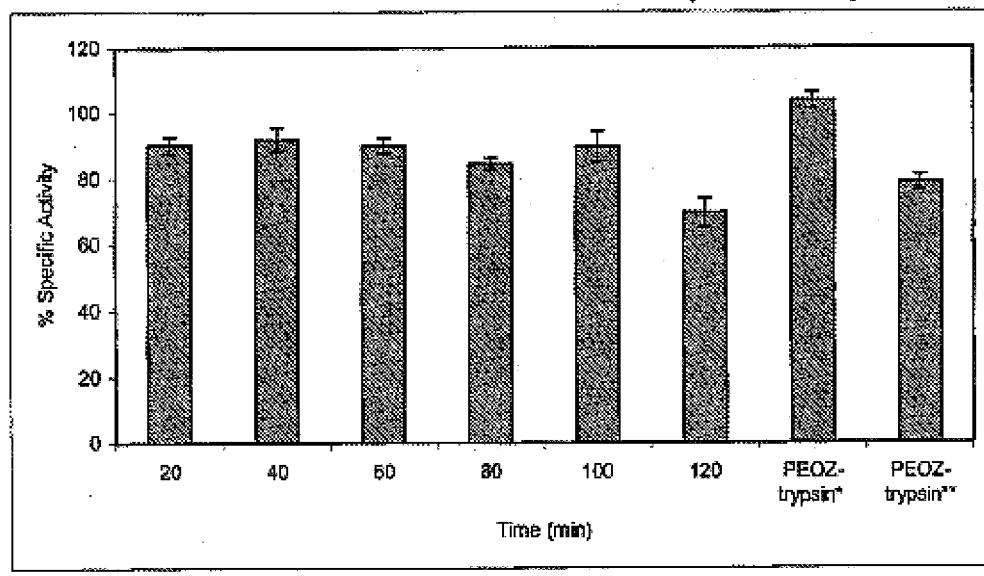
FIG. 8 is a graph showing the effect of time under an electric field on enzyme activity.

To investigate the effect an electric field plays in enzyme activity after electrospinning, PEOZ-spun trypsin activity was measured after different time intervals of applying an electric field on a trypsin-containing polymer solution. The fiber was collected after 20, 40, 60, 80, 100, and 120 minutes of electrospinning. Also, the activity was measured directly after the preparation of trypsin-containing polymer solution and after 120 min under electric field without forming the fiber. Fixed concentrations of trypsin (2.5 mg/ml, 0.25% w/v) and PEOZ (26% w/v) were used, and electrospinning was done under the conditions described above for PEOZ. The residual enzyme activity, expressed as a percent of the rate obtained for the native trypsin, is plotted in FIG. 8 as a function of time under electric field during electrospinning. Samples labeled PEOZ-trypsin* were measured directly after preparation of PEOZ-trypsin solution; PEOZ-trypsin** activity was the activity measured from a solution after 120 min under electric field without forming the fiber. All samples retained greater than 60 percent activity compared to native enzyme.

Figure 9:
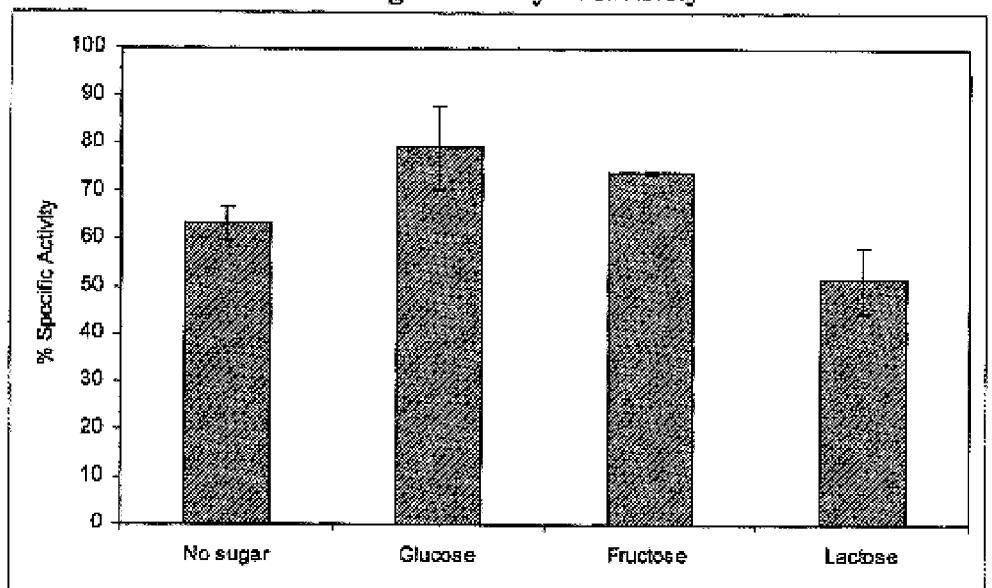
FIG. 9 is a graph showing the effect of the presence of sugar on enzyme activity.

The effect of three different sugars on enzyme activity recovered from trypsin-containing PEOZ fibers was also determined. Fixed concentrations of trypsin (2.5 mg/ml, 0.25% w/v) and PEOZ (26% w/v) were supplemented with 0.1 M glucose, 0.1 M fructose, or 0.1 M lactose, in the preparation of trypsin-containing PEOZ solution. Fibers were electrospun from these solutions and subsequently dissolved in distilled water as described above. The resulting enzyme activity was determined as also previously described. The residual enzyme activity, expressed as a percent of the rate obtained for the native trypsin, is plotted as a function of sugar type present in FIG. 9. As shown in FIG. 9, samples containing glucose or fructose retained greater activity than samples containing lactose.

The effect of three different concentrations of glucose and fructose on enzyme activity recovered from trypsin-containing PEOZ fibers was also determined. Fixed concentrations of trypsin (2.5 mg/ml, 0.25% w/v) and PEOZ (26% w/v) were used, and the electrospinning and recovery of enzyme from the resulting fibers was performed as previously described above. As shown in Table 6, increasing the amount of sugar during the preparation of trypsin-containing PEOZ solution did not greatly effect the enzyme activity.

TABLE 6

Effect of Sugar Feeding on Trypsin Activity

| Glucose | | Fructose | |
| --- | --- | --- | --- |
| Feed molar ratio (PEOZ:Glucose) | % Specific Activity* Mean ± SD | Feed molar ratio (PEOZ:Fructose) | % Specific Activity* Mean ± SD |
| 100:0 | 85.66 ± 2.90 | 100:0 | 52.42 ± 10.90 |
| 90:10 | 87.95 ± 8.58 | 90:10 | 65.41 ± 03.28 |
| 80:20 | 78.74 ± 8.97 | 80:20 | 68.19 ± 13.46 |
| 70:30 | 80.70 ± 4.83 | 70:30 | 68.89 ± 07.32 |

*Calculated on the basis of specific activity values compared with that of native trypsin (100%).

Trypsin-containing fibers were electrospun from trypsin-containing PEOZ solutions that were supplemented with polyethleneimine (PEI, Mw 2,000) or polyethylene glycol (PEG, Mw 10,000). Fixed concentrations of trypsin (2.5 mg/ml, 0.25% w/v) and PEOZ (26% w/v) were used, the electrospinning was done under the above described conditions for PEOZ, and the enzyme activity was determined as described above. As shown in Table 7, by increasing the PEI ratio, the retained enzyme activity increased from approximately 47 percent to approximately 49 percent, to approximately 66 percent, and finally, to approximately 76 percent, compared with that of native trypsin. In contrast, by increasing the PEG ratio, the retained enzyme activity decreased compared to native trypsin.

TABLE 7

Effect of Additional Polymer on Retained Trypsin Activity

| PEI | | PEG | |
| --- | --- | --- | --- |
| Feed molar ratio (PEOZ: PEI) | % Specific Activity Mean ± SD | Feed molar ratio (PEOZ: PEG) | % Specific Activity Mean ± SD |
| 100:0 | 46.90 ± 12.22 | 100:0 | 67.51 ± 02.72 |
| 90:10 | 48.59 ± 06.13 | 90:10 | 77.00 ± 04.79 |
| 80:20 | 65.72 ± 02.72 | 80:20 | 61.91 ± 22.53 |
| 70:30 | 75.53 ± 02.55 | 70:30 | 38.62 ± 07.51 |

Figure 10:
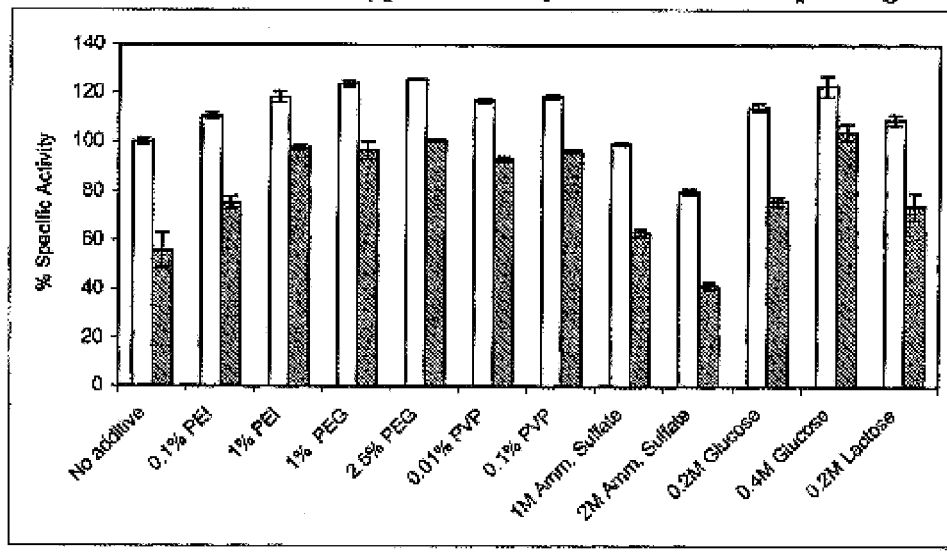
FIG. 10 is a graph showing the effect of the presence of additives on enzyme activity without electrospinning.

The effect of various additives on retained trypsin activity was examined. Trypsin was mixed with an additive in phosphate buffer to obtain a solution with 10 µg/ml enzyme, 0.067 M phosphate buffer, pH 7.0, and the desired concentration of additive. The solution was distributed in several vials (1 ml in each), which were closed tightly and sealed with parafilm to avoid undue evaporation of liquid. The samples were stored at 25° C. in an incubator together with an open container of water. After 10 days, sample vials were removed, cooled on ice and further allowed to equilibrate at room temperature before analysis for residual trypsin activity. Additives used were PEI (Mw 2000, 0.1 and 1% w/v), PEG (Mw 1000, 01 and 2.5% w/v), PVP (Mw 360000, 0.01 and 0.1% w/v), Ammonium Sulfate (1 and 2 M), Glucose (0.2 and 0.4 M), and 0.2 M Lactose. Results are shown in FIG. 10. The residual enzyme activity, expressed as a percent of the rate obtained for the native trypsin without additive, is plotted as a function of additive type that has been used. The open and filled columns represent the percentage of trypsin activity of the samples before and after the storage period, respectively. For all additives except 2M ammonium sulfate, activity prior to storage was comparable to trypsin without an additive present. Trypsin activity after storage was as high or higher for samples containing an additive, compared to the no additive sample, with the exception of the sample containing 2M ammonium sulfate.

Figure 11:
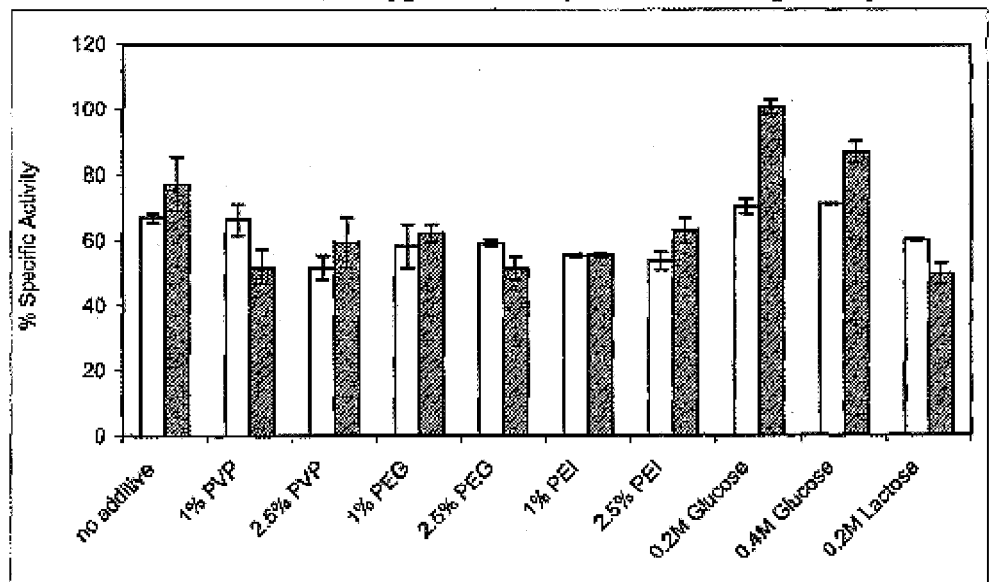
FIG. 11 is a graph showing the effect of the presence of additives on enzyme activity with electrospinning.

Trypsin-containing PEOZ fibers containing different additives, including PEI (Mw 2000, 1 and 2.5% w/v), PEG (Mw 1000, 1 and 2.5% w/v), PVP (Mw 360000, 1 and 2.5% w/v), Glucose (0.2 and 0.4 M), and 0.2 M Lactose, were also prepared. Fixed concentrations of trypsin (2.5 mg/ml, 0.25% w/v) and PEOZ (26% w/v) were used, and the electrospinning was done as described above except for samples containing PEI or lactose, in which a higher voltage, about 25 KV, was used and hence, the current was changed to 400 nA. The trypsin-containing PEOZ fiber was distributed in several vials (about 50 mg in each), which were closed tightly and sealed with parafilm to prevent contamination. The samples were stored at 25° C. in an incubator together with an open container of water. After 15 days, sample vials were removed; the fiber was dissolved in distilled water, cooled on ice and further allowed to equilibrate at room temperature before analysis for residual trypsin activity. Results are shown in FIG. 11. The residual enzyme activity, expressed as a percent of the rate obtained for the native trypsin, is plotted as a function of additive type that has been used. Assays were performed in 0.067 M phosphate buffer, pH 7.0, containing in a final volume of 3.2 ml, 0.25 mM BAEE and 0.625 µg/ml trypsin. The open and filled columns represent the percentage of trypsin activity of the samples before and after storage period, respectively. All samples tested retained at least approximately 50 percent trypsin activity over the length of the experiment (15 days).

Figure 12:
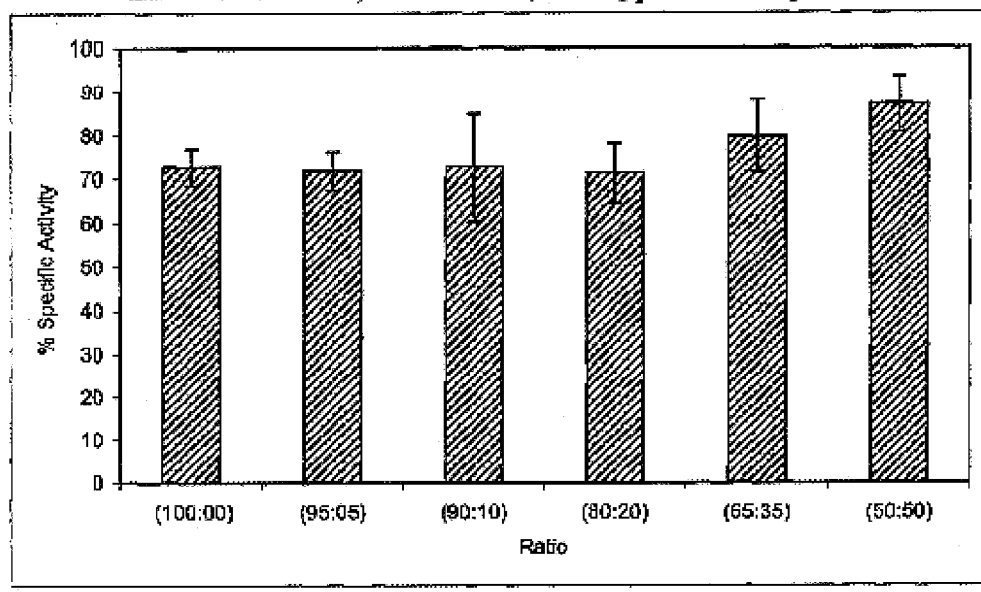
FIG. 12 is a graph showing the effect of use of ethanol as a solvent on enzyme activity.

Ethanol solutions were also used as a solvent in trypsin-containing PEOZ solutions with different molar ratios ($H_2O$: Ethanol; 95:05, 90:10, 80:20, 65:35, and 50:50). Fixed concentrations of trypsin (2.5 mg/ml, 0.25% w/v) and PEOZ (26% w/v) were used to electrospin fibers under the conditions described above for PEOZ solutions except with the higher molar ratios of ethanol, in which cases lower voltages were used. For the 65:35, $H_2O$: ethanol solution, 17 KV, and 140 nA were used. For the 50:50, $H_2O$: ethanol solution, 10 KV, and 20 nA were used. Enzyme activity was determined as described above. In FIG. 12, the specific activity of each sample after electrospinning and rehydration is plotted as a function of the molar ratio of water to ethanol, expressed as a percentage of the specific activity of a sample of native trypsin. Electrospinning using an ethanol solution was found to take the same amount of time or more compared to water alone as a solvent. As shown in FIG. 12, the residual activity was improved in samples using a higher molar ratio of ethanol. Although the applicants do not wish to be bound to any particular theory of operation, it is believed this greater activity may be attributed to the use of a lower voltage during electrospinning for samples containing a higher concentration of ethanol and to dehydration by ethanol.

The catalytic activity of encapsulated PEOZ-spun trypsin was also investigated. About 0.25% w/v trypsin (2.5 mg/ml) in 26% w/v polymer solution was electrospun using a cone cap at room temperature, a voltage of 22 KV, a current of 270 nA, and positive polarity. The gap distance was 23 cm, and the sample was collected on a polyester net. Polycaprolactone (PCL, Mw 120,000) was used to encapsulate PEOZ-spun trypsin. Three layers were formed; PEOZ-spun trypsin was in the middle with a covering layer of water non-soluble polymer (PCL) spun on either side of the middle layer. A solution of about 16% w/v of PCL was electrospun with a voltage of 25 KV and a current of 30 nA. Thin layers of fibers were collected on the net.

A small piece of trypsin-containing fiber was sunk in 4 ml of distilled water at 4° C. for about 20 hours in order for the enzyme to be released, and then this solution was tested for enzyme activity and protein concentration with appropriate dilutions. Results are summarized in Table 8. Specific activity values are expressed as a percentage of the specific activity of native trypsin. The protein content is the amount of protein released after sinking the fiber in distilled water at 4° C. for about 20 hours. The amount of protein content is very small compared to the protein released by dissolving PEOZ-spun trypsin in the same amount of distilled water. As shown in Table 8, the residual activity of trypsin was almost the same after 15 days of incubation at +25° C.

TABLE 8

Encapsulated-spun trypsin activity before and after 15 days of incubation at +25° C.

|  | Before | After |
|---|---|---|
| % Specific activity | 54.28 ± 10.41 | 54.61 ± 6.00 |
| Protein content (μg/ml) | 32.91 ± 5.05 | 43.03 ± 4.93 |

The thermostability of trypsin stored as trypsin-containing PEOZ fibers was examined by incubating native and PEOZ-spun trypsin at −20° C., +4° C., and +25° C. for varying periods of time. Samples were incubated as aqueous and solid (fiber) states and were periodically withdrawn and tested for residual activity. Assays were performed in 0.067 M phosphate buffer, pH 7.0, 0.25 mM BAEE and 0.625 μg/ml trypsin, in a final volume of 3.2 ml. Results are shown in FIGS. 13–18. A clear improvement in storage stability at +25° C. was found in PEOZ-spun trypsin.

Figure 13:
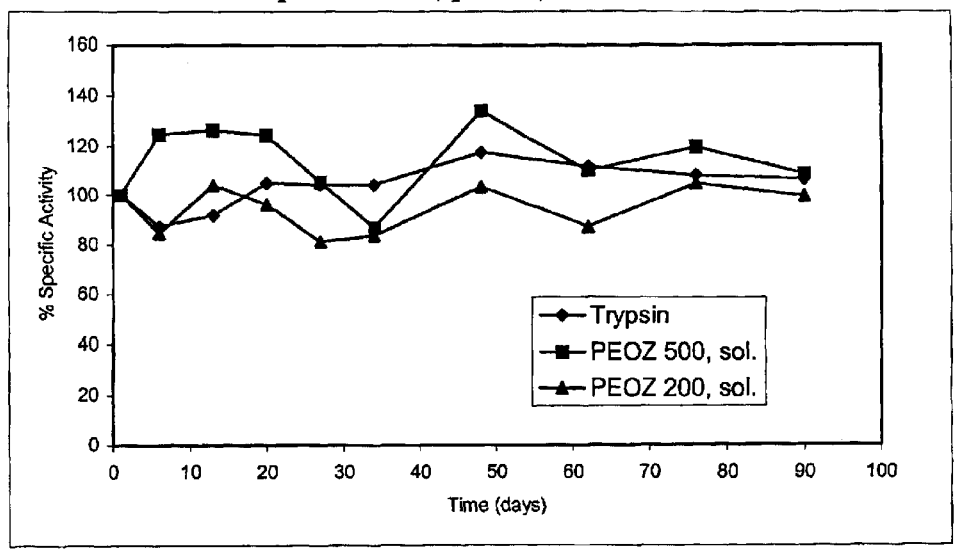
FIG. 13 is a graph showing the activity of native and PEOZ-spun trypsin after storage at −20° C. in an aqueous state.

FIG. 13 shows trypsin activity after long term storage of native and PEOZ-trypsin solution in an aqueous state, pH 7.8, at −20° C. The residual enzyme activity, expressed as a percent of the rate obtained for the enzyme at the first day, is plotted as a function of time. Samples were native trypsin (♦), PEOZ (Mw 500,000)-spun trypsin (■), and PEOZ (Mw 200,000)-spun trypsin (▲).

Figure 14:
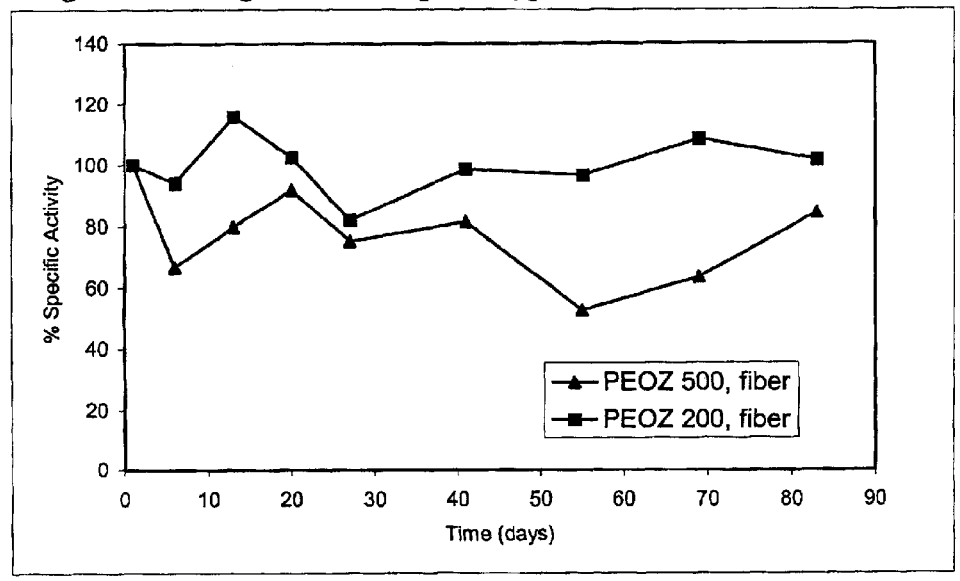
FIG. 14 is a graph showing the activity of PEOZ-spun trypsin after storage at −20° C. in a solid state.

FIG. 14 shows trypsin activity after long term storage of PEOZ-spun trypsin in solid state (fiber) at −20° C. The residual enzyme activity, expressed as a percent of the rate obtained for the enzyme at the first day, is plotted as a function of time. Samples were PEOZ (Mw 500,000)-spun trypsin (▲), and PEOZ (Mw 200,000)-spun trypsin (■).

Figure 15:
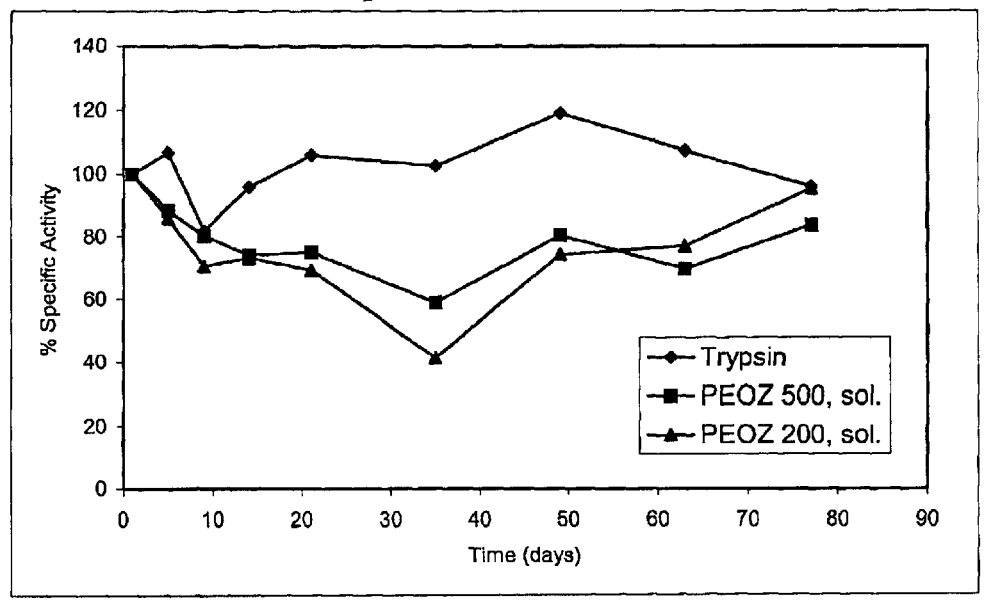
FIG. 15 is a graph showing the activity of native and PEOZ-spun trypsin after storage at 4° C. in an aqueous state.

FIG. 15 shows trypsin activity after long term storage of native and PEOZ-trypsin solution in an aqueous state, pH 7.8, at +4° C. The residual enzyme activity, expressed as a percent of the rate obtained for the enzyme at the first day, is plotted as a function of time. Samples were native trypsin (♦), PEOZ (Mw 500,000)-spun trypsin (■), and PEOZ (Mw 200,000)-spun trypsin (▲).

Figure 16:
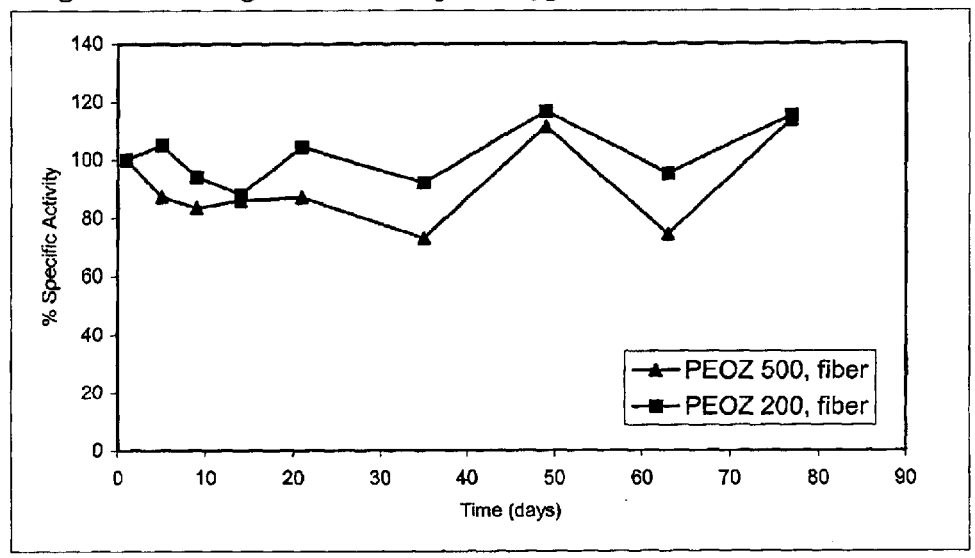
FIG. 16 is a graph showing the activity of PEOZ-spun trypsin after storage at 4° C. in a solid state.

FIG. 16 shows trypsin activity after long term storage of PEOZ-spun trypsin in solid state (fiber) at +4° C. The residual enzyme activity, expressed as a percent of the rate obtained for the enzyme at the first day, is plotted as a function of time. Samples were PEOZ (Mw 500,000)-spun trypsin (▲), and PEOZ (Mw 200,000)-spun trypsin (■).

Figure 17:
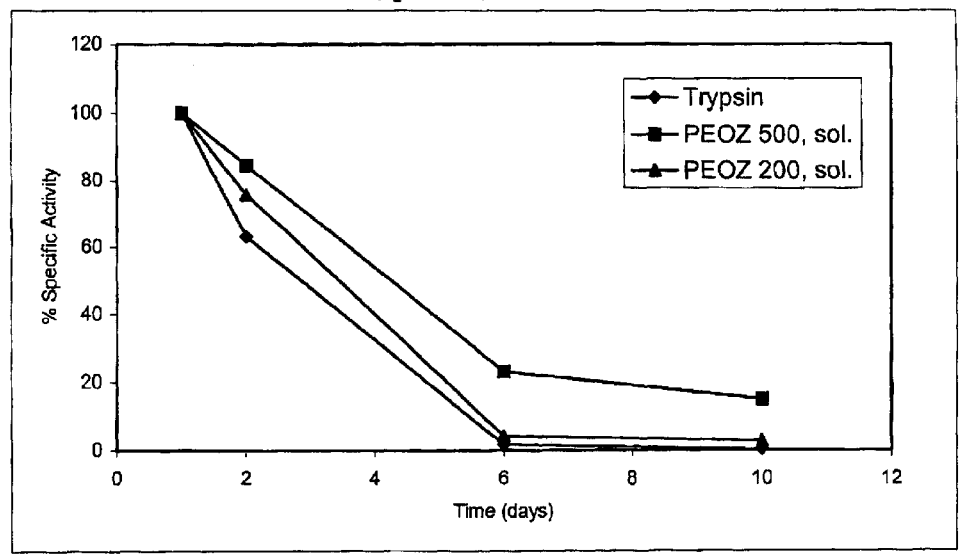
FIG. 17 is a graph showing the activity of native and PEOZ-spun trypsin after storage at 25° C. in an aqueous state.

FIG. 17 shows trypsin activity after long term storage of native and PEOZ-trypsin solution in an aqueous state, pH 7.8, at +25° C. The residual enzyme activity, expressed as a percent of the rate obtained for the enzyme at the first day, is plotted as a function of time. Samples were native trypsin (♦), PEOZ (Mw 500,000)-spun trypsin (■), and PEOZ (Mw 200,000)-spun trypsin (▲).

Figure 18:
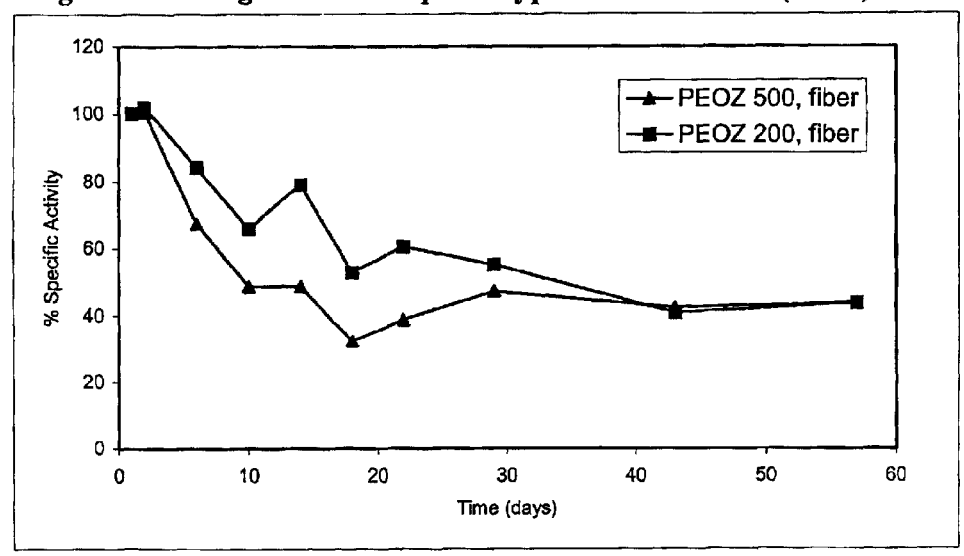
FIG. 18 is a graph showing the activity of PEOZ-spun trypsin after storage at 25° C. in a solid state.

FIG. 18 shows the residual enzyme activity, expressed as a percent of the rate obtained for the enzyme at the first day, plotted as a function of time. Samples were PEOZ (Mw 500,000)-spun trypsin (▲), and PEOZ (Mw 200,000)-spun trypsin (■).

Thrombin was used to test enzyme activity before and after being electrospun in a polymer solution. Activity of thrombin was determined by measuring the increase in the absorbance of a solution at 405 nm resulting from the release of p-nitroaniline from tosyl-glycyl-prolyl-arginine-4-nitranilide acetate sold under the tradename Chromozym-TH (Sigma Chemical Co., St. Louis, Mo.). The assay takes place in a buffer containing 0.01 M Hepes/0.01 M Tis-HCl, pH 7.4, 100 μM Chromozym-TH, 0.1 M NaCl, and 0.1 percent polyethylene glycol 6000.

The total volume of the reaction volume was 1 ml; the absorbance was read at 25° C. at a wavelength of 405 nm. One unit of enzyme is the amount of enzyme which leads to the release of 1 μmole p-nitroaniline (P-NA)/min/mt/mg at 25° C. Enzyme activity data is shown in Table 9.

TABLE 9

Thrombin Activity Before Electrospinning With PEOZ

| Sample | Enzyme Activity (ΔA405/min/mg/ml) |
|---|---|
| 1 | 6.6 |
| 2 | 6.4 |
| Mean ± SD | 6.5 ± 0.1 (n = 2) |

A 25 percent w/v solution that was 1.27 w/w percent thrombin to polyethyl oxazoline (PEOZ) was electrospun using a cap, at room temperature, a voltage of 26 kV, a current of 2 µA, and positive polarity. The gap distance was 15 cm, and the sample was collected on a polyester net. A thin layer of fiber was collected on the net. Spun PEOZ fibers containing dehydrated trypsin (about 5 cm×7 cm) were dissolved in 1 ml of distilled water. This solution was assayed for enzyme activity as described above with appropriate dilutions. Protein concentrations were determined using a Bradford assay (Bio-Rad Laboratories) with appropriate dilutions. Data for enzyme activity after electrospinning with polyethyl oxazoline (PEOZ) is shown in Table 10.

TABLE 10

Thrombin Activity After Electrospinning With PEOZ

| Sample | Enzyme Activity ($\Delta$A405/min/mg/ml) |
|---|---|
| 1 | 4.0 |
| 2 | 2.8 |
| 3 | 3.8 |
| Mean ± SD | 3.5 ± 0.5 (n = 3) |

The data from Tables 9 and 10 indicate that thrombin retains about 54 percent of its activity after electrospinning and subsequent rehydration (3.5/6.5×100=54 percent).

Stability of thrombin samples that were electrospun in PEOZ were tested after one week. Samples were electrospun and thrombin activity and protein concentration were determined as described above. These data are shown in Table 11.

TABLE 11

Thrombin Stability

| Time | Thrombin Specific Activity | Percent Activity Retained |
|---|---|---|
| Thrombin without spinning in PEOz | 6.48 ± 0.08 (n = 2) | — |
| Immediately | 3.54 ± 0.53 (n = 3) | 54.58 |
| One week | 6.81 ± 0.53 (n = 3) | 100+ |

A 2 percent solution of albumin in a 16.6 percent solution of PEOZ was spun into fibers by electrospinning. The sample was spun at room temperature using a cap, a voltage of 20 kV, a gap distance of 29 cm, a current of 1 µamp, and negative polarity. Fibers with a diameter of approximately 1 µm were successfully produced and deposited on a foil slide.

A solution of fluorescently labeled albumin in a solution of PEOZ was electrospun into fibers. The concentration of albumin was 12 percent (w/w) of the polymer. The sample was spun at room temperature using a pipette, a voltage of 12.1 kV, a current of less than 1 µampere, a gap distance of 16 cm, and negative polarity. Fibers were successfully produced and deposited on a foil slide and screen.

Figure 19:
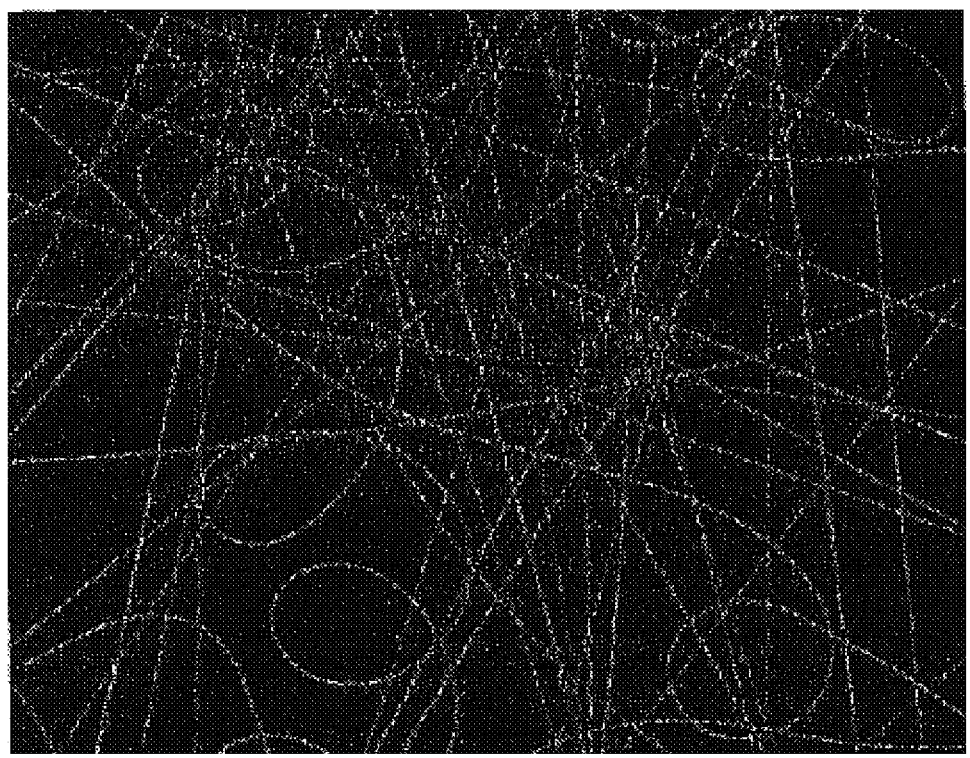
FIG. 19 is a photomicrograph showing fibers electrospun with fluorescently labeled albumin.

Another sample of fluorescently labeled albumin was spun in a 28 percent PEOZ solution (5 percent albumin: polymer, w/w) at room temperature, using a pipette, a voltage of 19.9 kV, a current of 0.5 µampere, a gap distance of 15 cm, and negative polarity. Fibers were successfully produced and deposited on a foil slide and screen. FIG. 19 shows a fluorescent photomicrograph of the resulting fibers.

Another sample of fluorescently labeled albumin was spun in a 28 percent PEOZ solution (5 percent albumin-:polymer w/w) at room temperature, using a pipette, a voltage of 20.8 kV, a current of approximately 1 µampere, a gap distance of 10 cm, and negative polarity. Fibers were deposited on a foil slide and screen.

Another sample of fluorescently labeled albumin was spun in a poly(ethyl-oxazoline-ethyleneimine) (PEOZ-EI) solution. The PEOZ-EI was 40 percent hydrolyzed polymer of PEOZ. Fluorescent albumin (4 percent w/w of total polymer used) was mixed with 20 percent (w/w) PEOZ-EI in 30 percent ethanol. Fibers were spun at room temperature with a voltage of 16 kV, >1 µampere of current, and a gap distance of 12 cm. The resulting fibers are water soluble as spun but may be crosslinked with a very small amount of cross-linking agent (as low as 1 percent). Fiber mats made with PEOZ-EI fibers are generally stronger than similar mats made from PEOZ fibers.

A sample of fluorescently labeled dextran having a molecular weight of approximately 4400 was spun in a 7 percent solution of polyvinyl pyrrolidone (4 percent dextran:polymer w/w) at room temperature, using a pipette, a voltage of 17.2 kV, a current of approximately 0.1 µampere, a gap distance of 20 cm, and negative polarity. Fibers were deposited on a foil slide. Another sample of fluorescently labeled dextran (4400 molecular weight) was spun in a 9 percent solution of polyvinyl pyrrolidone at room temperature, using a pipette, a voltage of 17.2 kV, a current of approximately 0.25 µampere, a gap distance of 20 cm, and negative polarity. Fibers with a diameter of less than 1 µm were deposited on a foil slide.

A sample of fluorescently labeled dextran having a molecular weight of approximately 260,000 was spun in a 24 percent solution of PEOZ (4.4 percent dextran:polymer w/w) at room temperature, using a pipette, a voltage of 18.6 kV, a current of approximately 0.3 µampere, a gap distance of 20 cm, and negative polarity. Fibers with a diameter of about 1–2 µm were deposited on a foil slide.

A sample of fluorescendy labeled peroxidase was spun in a 13 percent solution of PEOZ (2.1 percent peroxidase:polymer, w/w) at room temperature, using a pipette, a voltage of 17.2 kV, a current of approximately 0.2 µampere, a gap distance of 20 cm, and negative polarity. Fibers with a diameter of approximately 1 µm were deposited on a foil slide and screen.

Based upon the foregoing disclosure, it should now be apparent that electrospinning of biological materials with polymers will carry out the objects set forth hereinabove. It is, therefore, to be understood that any variations evident fall within the scope of the claimed invention and thus, the selection of specific component elements can be determined without departing from the spirit of the invention herein disclosed and described.

As used herein, the term "fiber" includes not only structures that are cylindrical, but also includes structures which vary from a cylindrical shape, such as for example, structures which are spherical, acicular, droplet shaped, or flattened or ribbon shaped. Other configurations are also possible. For example, the fiber of the present invention may appear "beaded" or otherwise vary from an entirely cylindrical configuration.

We claim:

1. A method of preserving a biological material in a dry protective matrix comprising the steps of:

providing at least one fiber-forming material;

mixing at least one biological material, and optionally, one or more additives, to the at least one fiber-forming material to form a mixture;

forming at least one fiber from the mixture, wherein the fiber has a diameter between about 0.3 nanometers and about 25 microns; and hardening and/or drying said at least one fiber to thereby provide a biological material embedded in a dry protective matrix.

2. The method according to claim 1 wherein the step of forming at least one fiber from the mixture comprises electrospinning the mixture.

3. The method according to claim 1, wherein the at least one fiber-forming material is selected from the group consisting of water soluble polymers.

4. The method according to claim 1, wherein the at least one fiber-forming material is selected from the group consisting of poly (vinyl pyrrolidone), polyethyl oxazoline, polyethylenimine, polyethylene oxide, and mixtures and copolymers thereof.

5. The method according to claim 1, wherein the at least one biological material is selected from the group consisting of proteinaceous compounds, carbohydrates, nucleic acids and mixtures thereof.

6. The method according to claim 1, wherein the preserved biological material retains at least 25 percent of its activity when stored at room temperature for at least 12 hours.

7. The method according to claim 1, wherein the preserved biological material retains at least 25 percent of its activity when stored at room temperature for at least 1 week.

8. The method according to claim 1, wherein the at least one fiber-forming material is provided in a solvent selected from the group consisting of water, alcohols, and mixtures thereof.

9. The method according to claim 1, wherein the at least one biological material is a protein.

10. The method according to claim 1, wherein the at least one biological material is an enzyme.

11. The method according to claim 1, wherein the at least one biological material is thrombin.

12. The method according to claim 1, wherein the at least one biological material is a component of a medical dressing.

13. The method according to claim 1, wherein the at least one biological material is selected from the group consisting of viral fusion inhibitors, hormone antagonists, and compounds which exert an effect on an organism by binding with a receptor molecule in vivo.

14. The method according to claim 1, wherein the at least one additive is present and is selected from the group consisting of poly(ethylenimine), polyethylene glycol, poly (vinylpyrolidone), carbohydrates, and mixtures thereof.

15. The method according to claim 1, wherein the at least one additive is present and is selected from the group consisting of poly(ethylenimine) at a concentration between about 1 and about 2.5 percent, polyethylene glycol at a concentration between about 1 and about 2.5 percent, poly (vinylpyrolidone) at a concentration between about 1 and about 2.5 percent, glucose at a concentration between about 0.2 and about 0.4 M, and lactose at a concentration of about 0.2 M and mixtures thereof.

16. A biological material preserved by the method according to claim 1.

17. A biological material according to claim 15, wherein the biological material is selected from the group consisting of proteinaceous compounds, carbohydrates, nucleic acids and mixtures thereof.

18. A biological material according to claim 15, wherein the biological material is capable of acting as an antigen.

19. A biological material according to claim 15, wherein the biological material is a component of a vaccine.

20. A biological material according to claim 15, wherein the biological material is a component of a kit for determining the presence of a biological or chemical compound.

21. A biological material according to claim 15, wherein the biological material is selected from the group consisting of viral fusion inhibitors, hormone antagonists, and compounds which exert an effect on an organism by binding with a receptor molecule in vivo.

22. A method of preserving a biological material comprising the steps of:

providing at least one fiber-forming material selected from the group consisting of poly (vinyl pyrrolidone), polyethyl oxazoline, polyethylenimine, polyethylene oxide, and mixtures and copolymers thereof;

mixing at least one biological material, and optionally, one or more additives, to the at least one fiber-forming material to form a mixture; and forming at least one fiber from the mixture, wherein the fiber has a diameter between about 0.3 nanometers and about 25 microns.

* * * * *